(12) United States Patent
Olson et al.

(10) Patent No.: US 9,968,757 B2
(45) Date of Patent: May 15, 2018

(54) MEDICAL KIT FOR FACILITATION OF CHANGING A URINARY CATHETER

(71) Applicant: MED TECH INVEST EUROPE AB, Bjärred (SE)

(72) Inventors: Johan Olson, Bjärred (SE); Johan Drott, Bjärred (SE); Gerd Nilsson, Landskrona (SE)

(73) Assignee: MED TECH INVEST EUROPE AB, Bjärred (SE)

( * ) Notice: Subject to any disclaimer, the term of this patent is extended or adjusted under 35 U.S.C. 154(b) by 482 days.

(21) Appl. No.: 14/438,438

(22) PCT Filed: Oct. 23, 2013

(86) PCT No.: PCT/SE2013/051231
§ 371 (c)(1),
(2) Date: Apr. 24, 2015

(87) PCT Pub. No.: WO2014/065748
PCT Pub. Date: May 1, 2014

(65) Prior Publication Data
US 2015/0283354 A1    Oct. 8, 2015

(30) Foreign Application Priority Data
Oct. 26, 2012   (SE) ...................................... 1251209

(51) Int. Cl.
*A61M 25/00*    (2006.01)
*A61M 25/01*    (2006.01)
(Continued)

(52) U.S. Cl.
CPC ....... *A61M 25/002* (2013.01); *A61M 25/0111* (2013.01); *A61M 25/0017* (2013.01);
(Continued)

(58) Field of Classification Search
CPC ............ A61M 25/0017; A61M 25/002; A61M 25/0045; A61M 25/0111; A61M 27/00;
(Continued)

(56) References Cited

U.S. PATENT DOCUMENTS 4,246,909 A * 1/1981 Wu .......................... A61F 5/44
128/DIG. 24
6,053,905 A * 4/2000 Daignault, Jr. .... A61M 25/0111
206/364
(Continued)

FOREIGN PATENT DOCUMENTS

CN    201026319 Y    2/2008
CN    201453746 U    5/2010
(Continued)

OTHER PUBLICATIONS

Japanese Search Report dated Jun. 9, 2017 received in Patent Application No. 2015-539555 (20 pages Japanese with English Translation).
(Continued)

*Primary Examiner* — Benjamin Klein
(74) *Attorney, Agent, or Firm* — Smith, Gambrell & Russell, LLP

(57) ABSTRACT

The present invention describes a medical kit 1 for facilitation of changing a urinary catheter in a patient, wherein the medical kit 1 comprises a first component in the form of a container 2 and a second component being a clamping unit 3 comprising two opposite clamping portions 4, 5, which container 2 and which clamping unit 3 are adapted to be reassembled so that the clamping unit 3 constitutes an end unit of the container 2 and clamping unit 3, and which clamping unit 3 allows for a catheter 6 to be pulled through and between the clamping portions 4, 5 where the clamping portions 4, 5 have a pressing effect on the catheter 6 but still allows for a sliding contact between the clamping portions (Continued)

4, 5 and the compressed catheter 6, allowing for gelatinization of a urethra from the inside out when a catheter 6 containing lubricant/anaesthetic gel is pulled out from the patient and through and between the clamping portions 4, 5, said catheter 6 intended to be contained in the container 2 during removal of the catheter 6 and after usage for a hygienic procedure.

13 Claims, 5 Drawing Sheets

(51) Int. Cl.
*A61M 39/28* (2006.01)
*A61M 27/00* (2006.01)

(52) U.S. Cl.
CPC ......... *A61M 25/0045* (2013.01); *A61M 27/00* (2013.01); *A61M 39/284* (2013.01); *A61M 2025/0046* (2013.01); *A61M 2210/1089* (2013.01)

(58) Field of Classification Search
CPC ........ A61M 39/284; A61M 2025/0046; A61M 2210/1089
See application file for complete search history.

(56) References Cited

U.S. PATENT DOCUMENTS

| | | |
|---|---|---|
| 6,578,709 B1 | 6/2003 | Kavanagh et al. |
| 7,476,223 B2 | 1/2009 | McBride |
| 2003/0018302 A1 | 1/2003 | Kavanagh et al. |
| 2007/0225649 A1 | 9/2007 | House |
| 2009/0099531 A1 | 4/2009 | Griesbach, III |

FOREIGN PATENT DOCUMENTS

| | | |
|---|---|---|
| CN | 201537303 U | 8/2010 |
| DE | 4141787 | 7/1993 |
| FR | 2794638 | 12/2000 |
| GB | 2284764 | 6/1995 |
| JP | S55-50370 A | 4/1980 |
| JP | H09-262290 A | 10/1997 |
| JP | 2004-535256 A | 11/2004 |
| JP | 2007-533331 A | 11/2007 |
| WO | 2011/019359 A1 | 2/2011 |
| WO | 2011/147803 A1 | 12/2011 |

OTHER PUBLICATIONS

Notification of Reasons for Refusal dated Jul. 6, 2017 received in Application No. 2015-539555 (6 pages with English Translation).
International Search Report for PCT/SE2013/051231 dated May 1, 2014 (5 pages).
Extended Search Report for EP 13 84 8880 dated Jun. 9, 2016 (7 pages).
Written Opinion of the International Searching Authority for International Application No. PCT/SE2013/051231, dated Feb. 3, 2014 (5 pages).
International Preliminary Report on Patentability for International Application No. PCT/SE2013/051231, dated Apr. 28, 2015 (6 pages).

* cited by examiner

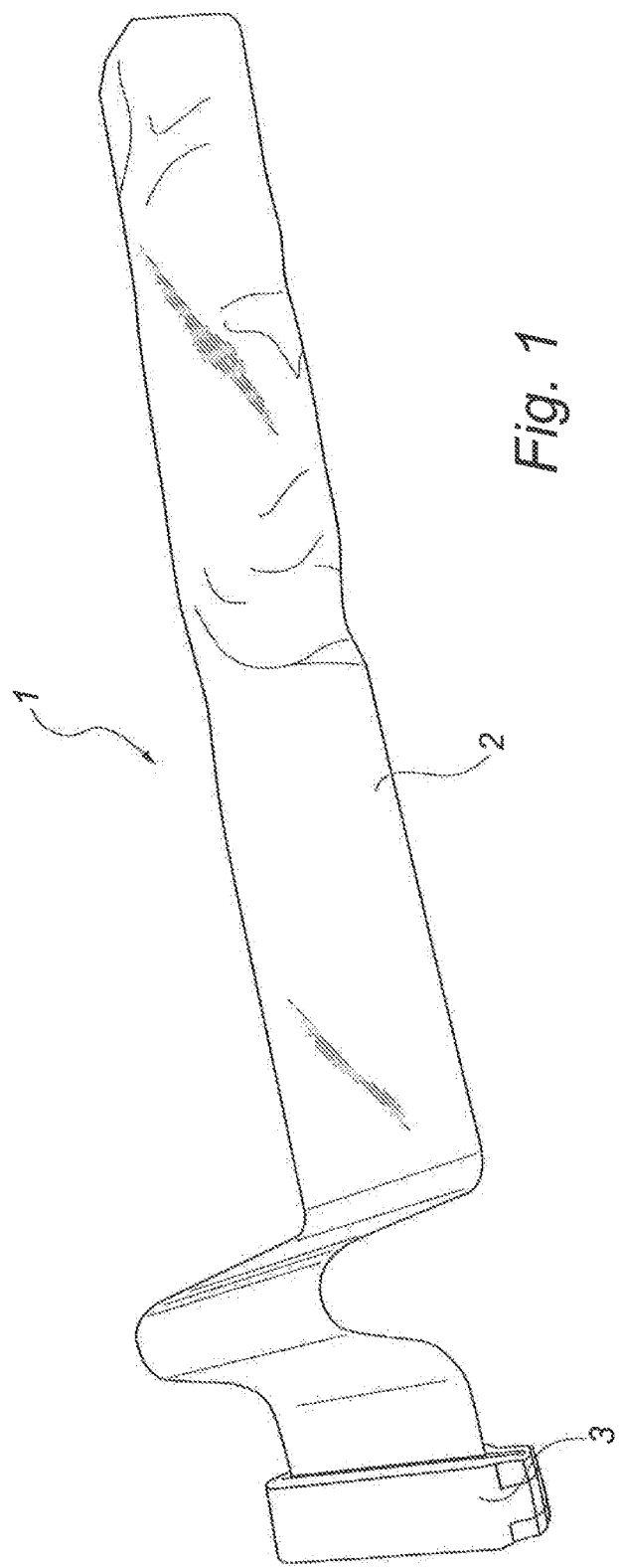

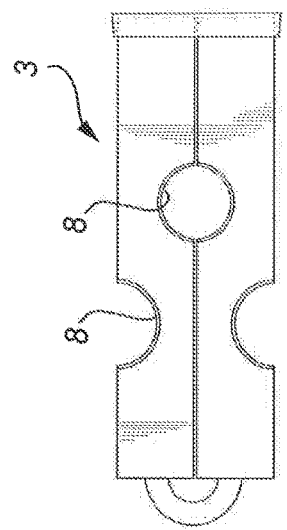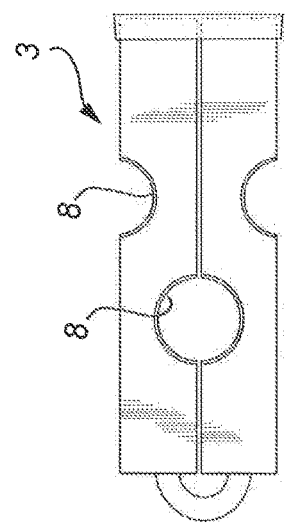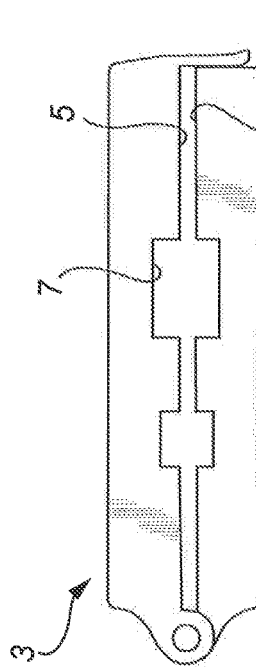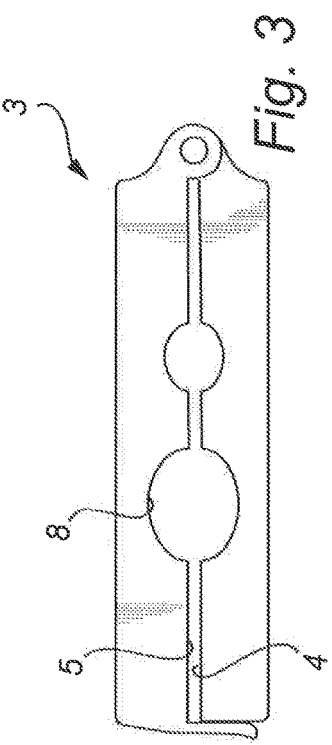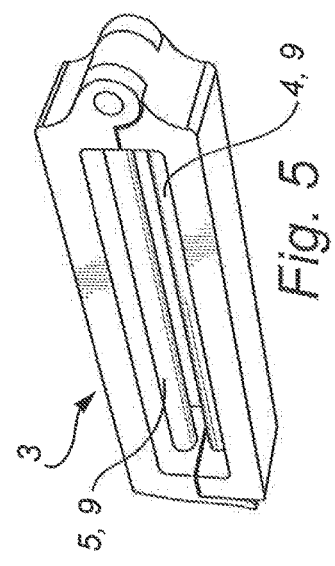

MEDICAL KIT FOR FACILITATION OF CHANGING A URINARY CATHETER

FIELD OF THE INVENTION

The present invention relates to a medical kit for facilitation of changing a urinary catheter in a patient.

TECHNICAL BACKGROUND

Different types of urinary catheters and systems therefore are known today. One such type is urinary catheters which are lubricated with a gel on their tip before being inserted.

The present invention is direct to a medical kit related to such urinary gel catheters and to a method for changing a urinary gel catheter in a patient.

One purpose of the present invention is to provide a medical kit which is easy and not time-consuming to use in comparison to existing products. Another purpose of the present invention is to provide a medical kit which is inexpensive to produce.

SUMMARY OF THE INVENTION

The stated purposes above are achieved by a medical kit for facilitation of changing a urinary catheter in a patient, wherein the medical kit comprises a first component in the form of a container and a second component being a clamping unit comprising two opposite clamping portions, which container and which clamping unit are adapted to be reassembled so that the clamping unit constitutes an end unit of the container and clamping unit, and which clamping unit allows for a catheter to be pulled through and between the clamping portions where the clamping portions have a pressing effect on the catheter but still allows for a sliding contact between the clamping portions and the compressed catheter, allowing for gelatinization of a urethra from the inside out when a catheter containing lubricant/anaesthetic gel is pulled out from the patient and through and between the clamping portions, said catheter intended to be contained in the container during removal of the catheter and after usage for a hygienic procedure.

The expression "are adapted to be reassembled" implies that the first and second components are either joined together (connected) during the production of the medical kit or are designed to be able to be joined together by the user. Furthermore, the fact that the second unit is a clamping unit implies that this unit has the inherent ability to be opened and closed by the user.

According to a first aspect of the present invention, the container is a bag, which is also shown in the figures discussed below.

In addition to the benefits presented above, there are also other advantages with the present invention. Firstly, the risk of contamination for a nurse or other medical personnel performing the change of a gel catheter is minimized. The bag component constitutes a protection containing the contaminated catheter. Secondly, the actual change of a catheter is easier to perform when using the kit according to the present invention. This is explained in more detail below.

It should be mentioned that there are medical devices known today which comprises a bag and a clamp. For instance, CN201026319 discloses a one-off and adjustable urine collection bag which is used by the patients who need to catheterize urine continuously. The utility model consists of a urine storage bag and a drainage tube, and is characterized in that an adjustable clamp is arranged on the drainage tube, which can be used to start or close a urethral catheter at any time to control the disheartenment of urine. As understood from above, the bag and clamp parts according to CN201026319 are different from these units according to the present invention. Furthermore, the purpose of these parts is also totally different.

Moreover, CN201453746 relates to a connection device used in bladder irrigation. In the connection device, one end of a communicating pipe is connected with the joint of a drainage bag, and an anti-skid groove is formed on the joint communicated with the communicating pipe; an adjustable clamp, which is said to be moved freely, is sleeved on the communicating pipe; the other end of the communicating pipe is connected to a vidian canal; the vidian canal is communicated with the communicating pipe; a screw joint, which can be screwed on or screwed off from the vidian canal, is mounted on the vidian canal; and a demountable protective cover of the drainage bag joint is sleeved on the drainage bag joint. The device is said to be well matched with a catheter, infusion apparatus or an injection syringe, and prevents liquid medicine and urine from leaking during bladder irrigation, so that a nursing staff and a bed sheet is not polluted.

Furthermore, in CN201537303 there is provided a urinary catheter fixation strap comprising a clamp, wherein a strip shaped fixation strap is arranged on the urinary catheter fixation strap and a hanging bag is arranged in the middle of the fixation strap and cohesive separable fastening fabrics are arranged on the positive and negative surfaces of the two ends and one clamp is arranged at one side of the hanging bag and a hook is arranged at another side and the clamp and hook are respectively fixed and connected with the fixation strap.

In the case of both CN201453746 and CN201537303 both design and purpose is different in comparison with the present invention.

BRIEF DESCRIPTION OF THE DRAWINGS

In FIG. 1 there is shown one embodiment of the medical kit according to the present invention.

In FIGS. 2, 3, 4a, 4b and 5 there are shown some different embodiments of the clamping unit according to the present invention.

Also

SPECIFIC EMBODIMENTS OF THE INVENTION

Figure 6:
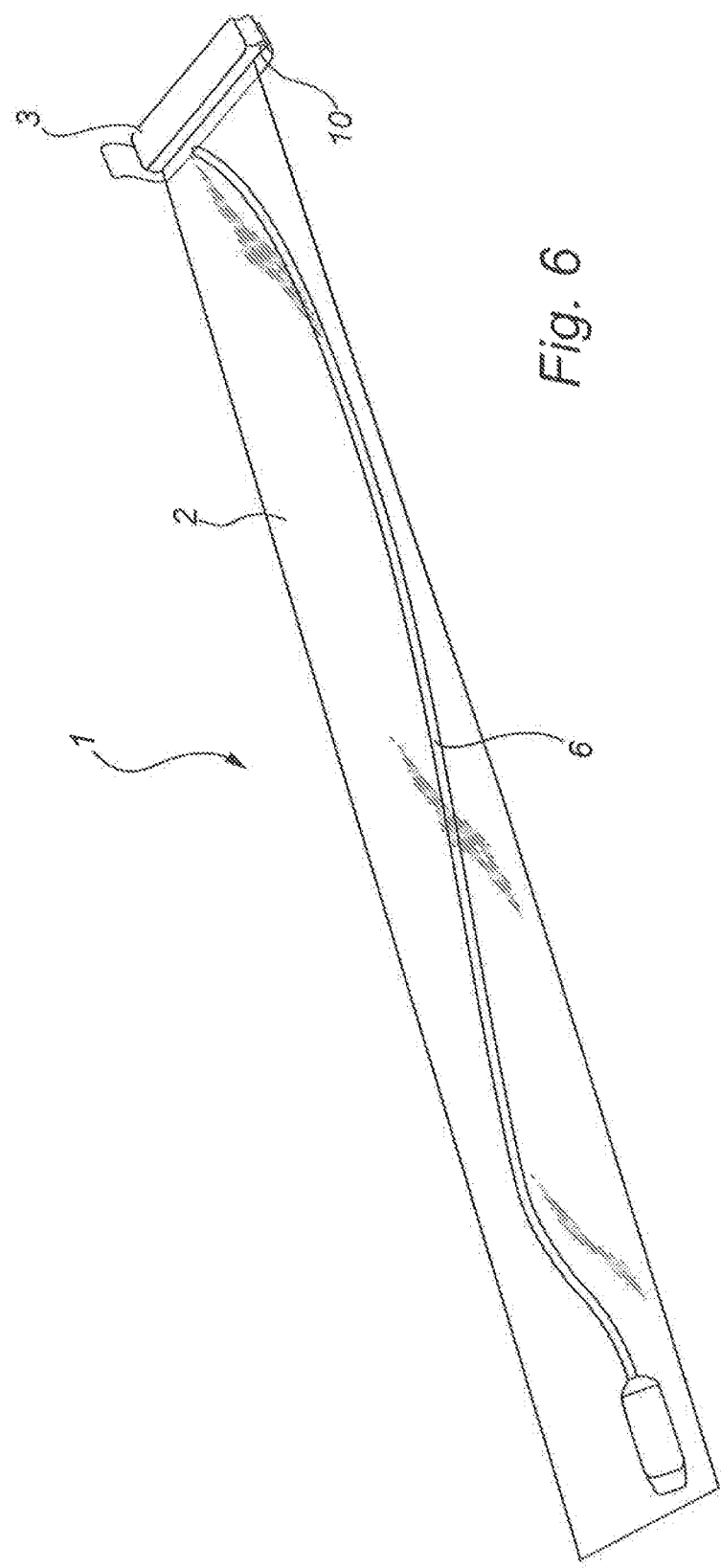
In FIG. 6 a similar kit as according to FIG. 1 is shown, however in this case a catheter is also contained.

Below, specific embodiment of the present invention will be discussed in more detail.

According to one specific embodiment of the present invention, the clamping unit is permanently fixated to the container, the container e.g. being a bag. One possible advantage of this design according to the invention is that the gel used is securely contained in the bag without any risk of leakage and contamination. It should, however, once again be mentioned that a two piece design where the clamping unit and bag is held separately until the user connects them is fully possible according to the invention. Furthermore, the design of the clamping unit may vary, and the ones shown in the drawings should only be seen as examples. For example a clamping unit having a handle, such as being a pair of tongs, is one alternative which is just as possible according to the present invention. It should be said that there are many different variants possible and the ones mentioned above and shown in the drawings are only examples.

According to another embodiment, at least one of the two opposite clamping portions comprises compartments. Only one of them or both may have one or several compartments according to the present invention. Furthermore, the compartments may have different size, as shown in some of the figures. The compartment is intended as a slot in which the catheter is situated. The design with compartments is intended to increase the possibility to pull the catheter between the clamping portions with a sliding contact but where a compression is exerted on the catheter.

According to one specific embodiment of the present invention, at least one of the two opposite clamping portions comprises concave portions. Also in this case one or both of the clamping portions may have the concave portions. When both of them have such concave portions, the formed hole of the clamping unit is "eye shaped". This may be beneficial to fixate the catheter hose in the middle of the hole. As seen in some of the figures, the formed holes may also be quadratic or rectangular or any other such shape. Furthermore, several holes of different size may be provided in one clamping unit to hold catheters of different size.

According to one other embodiment, at least one of the two opposite clamping portions is a roll. This is shown in FIG. 5, where each clamping portions is a roll. Such rolls are intended to ensure a sliding contact but should also compress the catheter. The rolls may e.g. be spring loaded to ensure a sliding and compressive effect.

Moreover, according to one embodiment, at least one of the two opposite clamping portions has a bevelled surface. As may be understood, this does not have to be as rolls such as according to FIG. 5, but instead with only the surface being bevelled. This is also provided to increase the sliding effect. Furthermore, according to one specific embodiment, at least a surface portion of each of two opposite clamping portions is made of a slide promoting material. This is also a design provided for increased sliding effect. Suitably, the entire contact surface is made of such a material. Many different types of materials are possible, e.g. soft rubber materials, for such slide promoting materials.

According to yet another specific embodiment, the clamping unit has a hinged end portion allowing opening and closing of the clamping unit. In such a design, the clamping unit may be closed both left and right. According to one embodiment, such a clamping unit may have a formed hole of one size when closed to the left, and one hole of another size when closed to the right. As such catheters of different size may be used with such a hinged clamping unit.

Also other components may be provided in a medical kit according to the invention. According to one embodiment, the medical kit also comprises a catheter and gel.

According to one embodiment, the container (bag) is at least as long as the catheter. The bag should of course be large enough to contain a catheter. Many catheters are wider at one end as they have a connection at this end, the connection intended to be connected to e.g. a gel syringe or the like.

Figure 8:
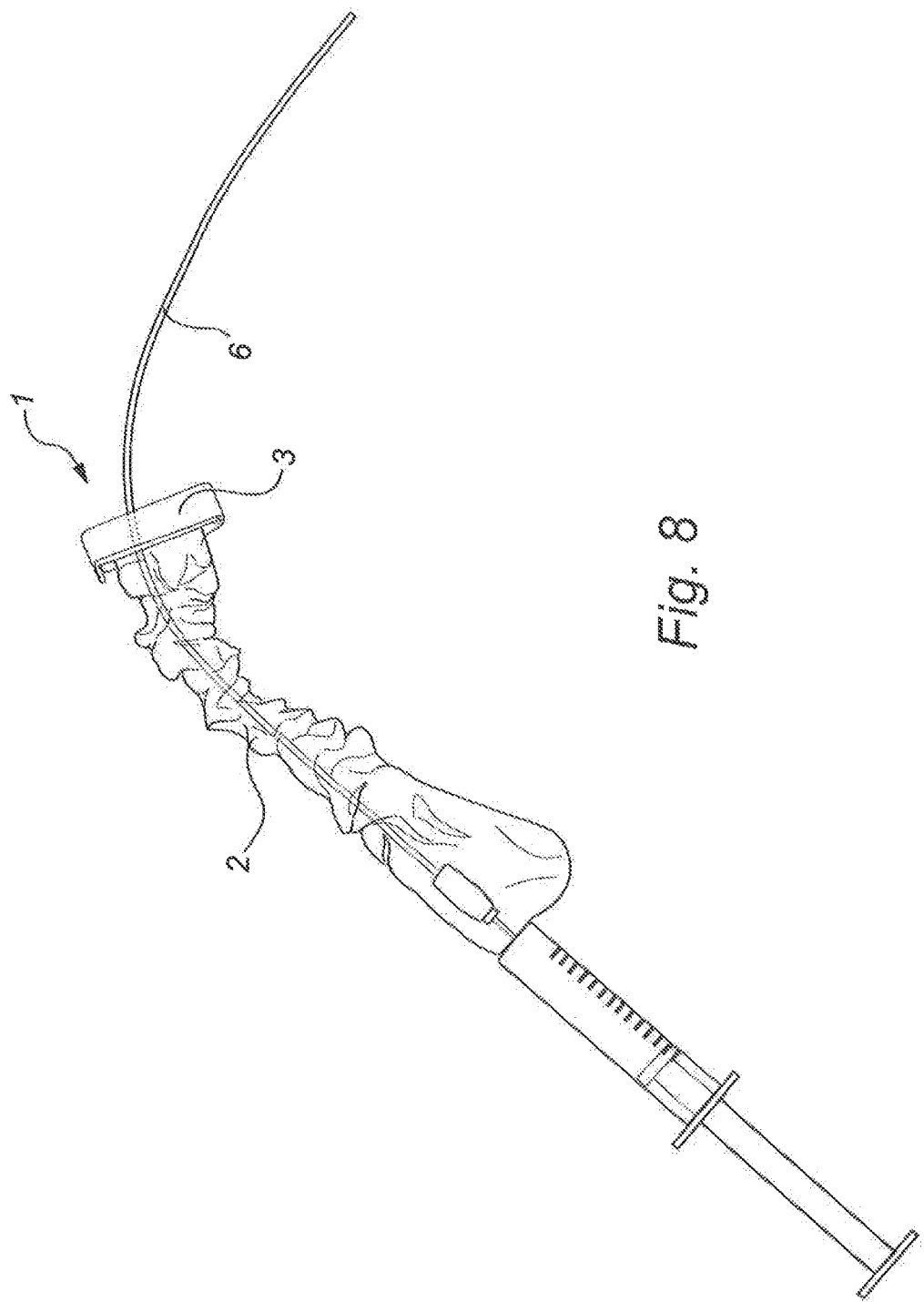
FIG. 8 shows such use of a medical kit, however in this case a syringe is connected to the catheter.

Moreover, according to yet another embodiment, the container (bag) also comprises a gel container intended to be connected to the catheter and punctured before use. The bag may be provided with holes or a connection device so that it is possible to gelatinize after the bag has been threaded over the end of the catheter. This design assures less risk for contamination and an easier usage. In a case according to above, the gel container may be provided as a separate compartment of the bag. According to another embodiment, the medical kit comprises a separate gel container, e.g. in the form of a gel syringe as shown in FIG. 8.

According to yet another specific embodiment, the gel container contains 7 ml lubricant/anaesthetic gel or less. The amount of lubricant/anaesthetic gel may of course vary according to the present invention, such as in proportion to the inner volume of the catheter. As said above, the amount of lubricant/anaesthetic gel may vary according to the present invention, e.g. in correspondence to the inner volume of the catheter, which in turn is dependent of the diameter and length of the catheter. Today it is usual to use two syringes containing about 10 ml of gel each. Thus, according to the present invention the amount of gel needed to be used may be decreased.

Furthermore, according to one specific embodiment of the present invention, the medical kit is arranged to create a ratio for the amount of lubricant/anaesthetic gel being pushed out from the catheter during removal of the catheter. The creation of ratio implies that more lubricant/anaesthetic gel is pushed out from the catheter than otherwise possible to generate just by having a compressive force from the clamping unit. This may be of interest as the volume of the urethra is larger than the catheter being used. According to one specific embodiment of the present invention this effect may be possible to achieve by providing a pressure inside of the catheter when the same is being pulled out of the patient. As such, the means for this feature may be provided in the separate gel container of the medical kit according to the present invention. Also other alternatives are possible according to the present invention.

PROCEDURE

Today the catheterization is normally performed according to the following. After appropriate investigation and pre-steps, gel is applied on the tip of a catheter and in the urethra. The gel is allowed to effect about 5 minutes. Thereafter, the catheter is fed into the urethra carefully. When a catheter is changed for a new one, the old one is first removed and a new one is applied according to above.

The present invention is directed to the change of a gel catheter. According to the present invention there is also provided a method for gelatinization of a urethra when a gel catheter is changed for another one in a patient, with a medical kit according to the present invention, wherein a catheter which is about to be changed for another one first is filled with lubricant/anaesthetic gel and wherein the gelatinization of the urethra then is performed from the inside out of the urethra when that catheter containing lubricant/anaesthetic gel is pulled out from the patient. The method according to the present invention has several advantages. Firstly, gel may be provided evenly inside of the urethra when the gelatinization is performed from the inside out. As such, it is also possible to use less amount of gel. Furthermore, as the present method and medical kit promote an evenly distribution of gel along the urethra per automatic, the procedure may be interrupted and then continued again without the need of starting the procedure from the beginning again, the latter being needed with procedures and aids present today.

Moreover, as the procedure involves use of the medical kit according to the present invention, it is also possible to minimize the risk of contamination. Furthermore, the time needed for a change of a catheter may be decreased in comparison with a standard procedure used today. For instance, as the medical kit and use thereof according to the present invention is not dependent of gravity for gel to be distributed along the urethra, both time and amount of gel are saved.

DETAILED DESCRIPTION OF THE DRAWINGS

In FIG. 1 there is shown a medical kit 1 comprising a container 2 in the form of a bag 2 and a clamping unit 3 having two opposite clamping portions 4, 5 (see FIGS. 2-5). The bag 2 and the clamping unit 3 are connected to each other, either permanently or connected before use.

The clamping unit 3 is an end unit of the device kit 1. The clamping unit 3 allows for a catheter 6 to be pulled through and between the clamping portions 4, 5, and the clamping portions 4, 5 have a pressing effect on the catheter 6 but also allows for a sliding contact between the clamping portions 4, 5 and the compressed catheter 6.

In FIG. 2 there is shown one embodiment of a clamping unit 3 according to the present invention. In this case the opposite clamping portions 4, 5 comprise compartments 7 providing one rectangular and one quadratic hole intended to hold the catheter 6 hose. In this case the opposite clamping portions 4, 5 have opposite situated compartments 7 providing the holes, but it should be understood that only one of the clamping portions 4, 5 also may have the compartments 7, and which in such case themselves hold the catheter 6 hose. Furthermore, only one hole may be provided to hold the catheter 6 hose, but two doles having different sizes and as such being suitable for different hose sizes may be of interest according to the present invention. Moreover, in this case the clamping unit 3 also has a hinged end portion (10) allowing opening and closing of the clamping unit 3. Such a hinged end portion may also allow for the clamping unit 3 to be closed both to the left and to the right.

In FIG. 3 there is shown another embodiment of a clamping unit 3 according to the present invention. In this case, the opposite clamping portions 4, 5 comprise concave portions 8 providing oblong holes. Also in this case two holes having different sizes are provided.

In FIGS. 4a and b there is shown another embodiment of a clamping unit 3 according to the present invention. This clamping unit 3 may be closed either to the right as shown in FIG. 4a, or to the left as shown in FIG. 4b. Depending on which, there are provided holes with different sizes. As notable, the hole provided in FIG. 4a is smaller than the hole provided in FIG. 4b. Moreover, in this case the endings are designed differently. As notable, the clamping unit 3 may be closed both to the left and right.

In FIG. 5 there is shown another embodiment of a clamping unit 3 according to the present invention. In this case, the two opposite clamping portions 4, 5 are rolls 9.

In FIG. 6 a similar kit as according to FIG. 1 is shown, however in this case a catheter 6 is also contained.

Figure 7:
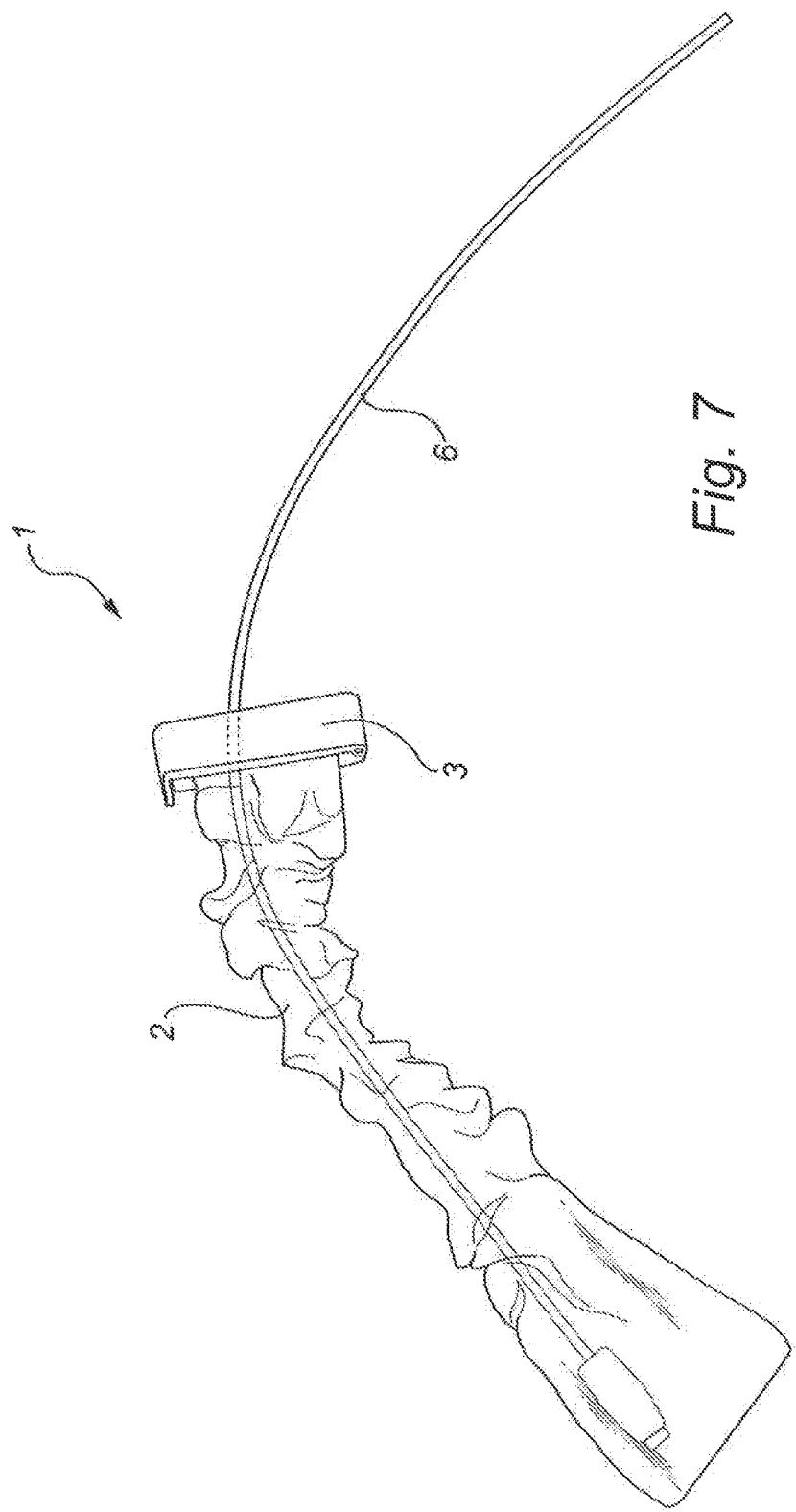
In FIG. 7 a medical kit according to the present invention during actual use is shown.

In FIG. 7 a medical kit according to the present invention during actual use is shown.

Also FIG. 8 shows such use of a medical kit, however in this case a syringe is connected to the catheter.

The invention claimed is:

1. A method for gelatinization of a urethra when a gel catheter is changed for another one in a patient, with a medical kit for facilitation of changing the gel catheter in a patient, wherein the medical kit comprises a catheter, a gel, a container and a clamping unit comprising two opposite clamping portions, the clamping unit being operable to allow the catheter to be pulled through and between the clamping portions with the clamping portions having a pressing effect on the catheter that allows for a sliding contact between the clamping portions and the compressed catheter, allowing for gelatinization of a urethra from the inside out when the catheter containing lubricant and/or anaesthetic gel is pulled out from the patient and through and between the clamping portions, said catheter being adapted for containment in the container during removal of the catheter and after usage for a hygienic procedure, and wherein the method comprises filling the catheter with lubricant and/or anaesthetic gel, and then performing gelatinization of the urethra from the inside out of the urethra when that catheter containing the lubricant and/or anaesthetic gel is pulled out from the patient.

2. The method according to claim 1, wherein the container is a bag.

3. The method according to claim 1, wherein the clamping unit is permanently fixated to the container.

4. The method according to claim 1, wherein at least one of the two opposite clamping portions comprises compartments.

5. The method according to claim 1, wherein at least one of the two opposite clamping portions comprises concave portions.

6. The method according to claim 1, wherein at least one of the two opposite clamping portions is a roll.

7. The method according to claim 1, wherein the clamping unit has a hinged end portion allowing opening and closing of the clamping unit.

8. The method according to claim 1, wherein at least one of the two opposite clamping portions has a bevelled surface.

9. The method according to claim 1, wherein at least a surface portion of each of two opposite clamping portions is made of a slide promoting material.

10. The method according to claim 1, wherein the container is at least as long as the catheter.

11. The method according to claim 1, wherein the container also comprises a gel container adapted for connection to the catheter and for puncture before use.

12. The method according to claim 1, wherein the medical kit comprises a separate gel container.

13. The method according to claim 11, wherein the gel container contains 7 ml or less of lubricant and/or anaesthetic gel.

* * * * *